United States Patent [19]

Francis

[11] Patent Number: 4,905,789
[45] Date of Patent: Mar. 6, 1990

[54] MUFFLER FOR BLOWER OF AIR DUCTWORK SUPPLY LINE

[76] Inventor: Monte D. Francis, P.O. Box 50094, Indianapolis, Ind. 46250-0094

[21] Appl. No.: 144,117

[22] Filed: Jan. 15, 1988

[51] Int. Cl.$^4$ .............................................. F01N 1/24
[52] U.S. Cl. .................................... 181/224; 181/225; 181/229; 181/238; 181/252
[58] Field of Search ............... 181/230, 224, 229, 232, 181/238, 239, 240, 252, 256, 202, 225, 277

[56] References Cited

U.S. PATENT DOCUMENTS

| | | | |
|---|---|---|---|
| 2,625,234 | 1/1953 | Fina ...................................... | 181/239 |
| 2,731,194 | 1/1956 | Kent .................................. | 181/225 X |
| 3,581,494 | 6/1971 | Scheitlin .......................... | 181/240 X |
| 3,884,037 | 5/1975 | Barber et al. ................... | 181/252 X |
| 4,264,282 | 4/1981 | Crago .............................. | 181/202 X |

*Primary Examiner*—B. R. Fuller
*Attorney, Agent, or Firm*—Robert A. Spray

[57] ABSTRACT

A muffler for minimizing the noise emanating from a blower of an air ductwork supply line, providing that the overall length of the muffler, and the insert length of the remote muffler outlet, are provided as functions of the wave length of the pitch of the whining noise caused by the blower's impeller; and the interior longitudinal wall of the muffler's end-wall are lined with sound-absorbing material.

14 Claims, 1 Drawing Sheet

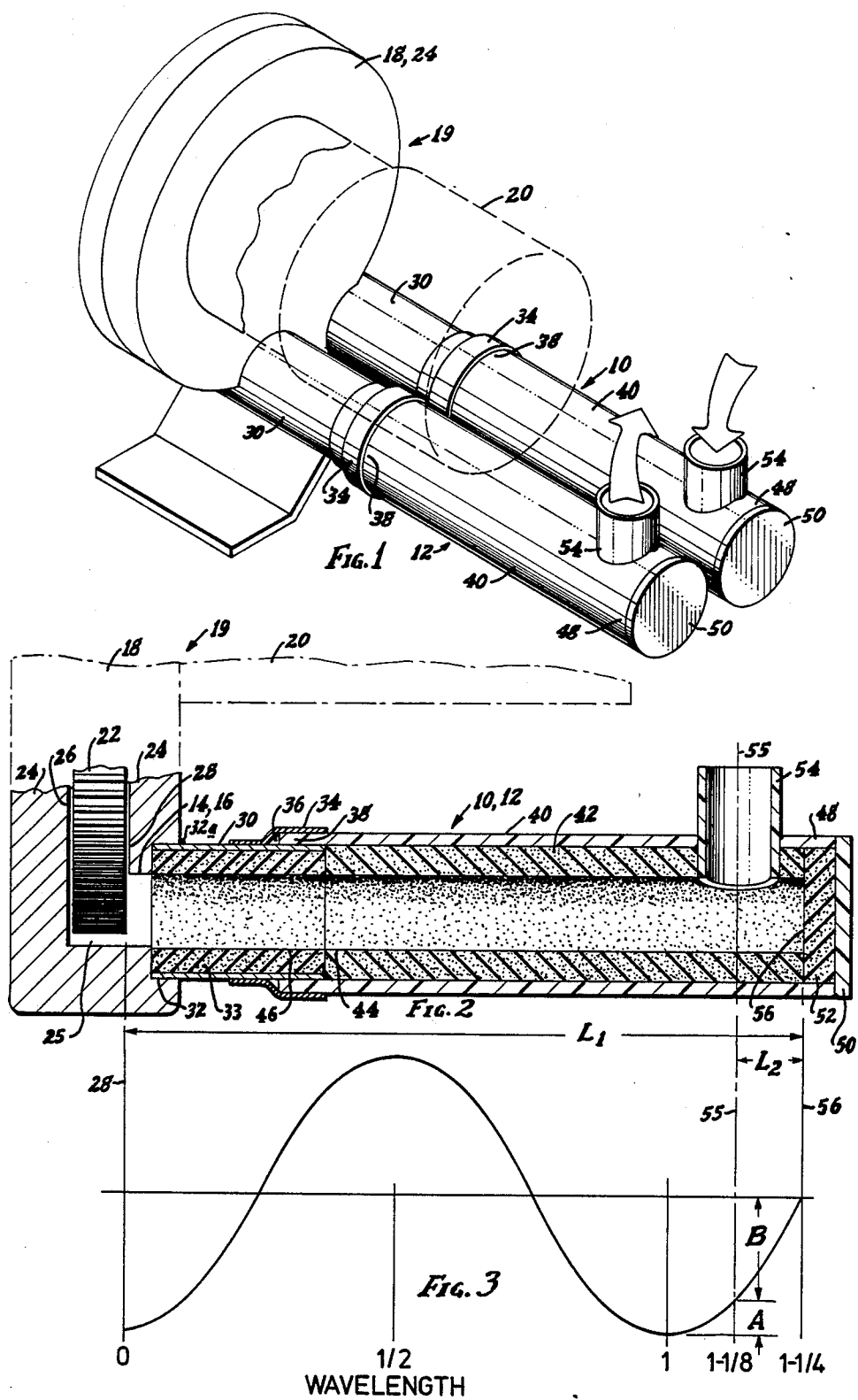

MUFFLER FOR BLOWER OF AIR DUCTWORK SUPPLY LINE

FIELD AND BACKGROUND OF THE INVENTION

The present invention relates to airduct mufflers, and more particularly to mufflers in systems particularly useful to provide assisted breathing for those persons who need a forced-breathing therapy, and more particularly as primarily now considered the dispensing of air to a person having respiratory problems such that air under pressure is forced upon the patient in alleviating his distress and breathing difficulties.

Even more particularly, as presently considered, equipment of the type of this invention is especially considered for use in the treatment and distress-relieving of a disease known as apnea, which is a respiratory disorder in which patients fail to breathe sufficiently or properly during sleep, recognized types being obstructive sleep apnea and central sleep apnea.

These are dreadful conditions, sometimes even life-threatening, and at least can cause devastating effects of changes of personality, family life problems, diminished work performance, irritability, impotence, insomnia, memory loss, etc., as the patient undergoes the loss of breathing repeatedly during sleep, even a minimum of such episodes to be considered as a medically significant being more than five episodes of cessation of airflow for at least ten seconds each, per hour of sleep.

Any other respiratory problem complicates the condition.

Tracheotomy, tonsillectomy, and uvulopalatopharyngoplasty, and combinations thereof, have been used to try to surgically correct the condition or alleviate the symptoms; and various drug therapies, and physical equipment such as rocking beds, iron lungs, body shells, and various ventilators have been tried.

Forms of ventilators known as CPAP (continuous positive airway pressure) have helped reduce the number of tracheotomies, these being devices with a blower/motor assembly, a flexible hose, and a tight-fitting nasal mask, by which air (sometimes with extra oxygen, and/or humidity control) is forced onto a patient, the pressure being always above atmospheric (i.e., "continuously positive"), thus above atmospheric during inhalation as well as exhalation.

And even though the use of CPAP ventilators is a significant bother and nuisance to a patient, it is better than many alternatives, so a patient has no realistic alternative to their use.

The above is given as an introduction to the long-recognized problems in this field, and the attempts to cure or relieve these problems, generally from the article "Broken Sleep", by Terrie Weaver and Richard P. Millman, as published in *American Journal of Nursing* (Feb., 1986) p. 146–150, having an extensive bibliography.

SPECIAL AND LONG-KNOWN NEED OF THIS INVENTION

As indicated above, the therapy of giving a patient forced breathing poses special needs, as now indicated.

In typical situations of forced breathing, for apnea sufferers, the over-atmospheric pressure is developed or provided by a bedside blower, or a pressure means within the room of the patient who is being helped by the forced-breathing apparatus; and apparently inevitably the blower operativity will be accompanied by an irritatingly noisy sound which is particularly objectionable to the attempted sleep of the patient.

The irritating noise is of course reduced as much as possible, such as by making sure that there is no mechanical squeaking noise of the blower's bearings, or rattle of the blower's housing, or noise otherwise from the mechanical aspects of the blower.

But, even with all such objectionable mechanical noise reduced to a minimum, even to an acceptable minimum, the pneumatic nature of the blower's operativity still has created a special whine-like noise effect which has been permitted even though it is also objectionable to many.

Patients have been forced to learn to "put up" with the pneumatically-related whining noise; and unless the patient is unusual, such as a person who seems to have no difficulty of going to sleep even with a ticking clock or with nearby loud snoring, or unless the patient wears some sort of ear-plugs, patients have found the pneumatically-caused whine quite objectionable.

Inherent factors of the distressing apnea problem make the pneumatic whine particularly objectionable. For one thing, the whine is at a high pitch which is considered irritating. Also, the very situation of this scene, i.e., the attempt to go to sleep, is the very occasion in which the patient will likely desire maximum quietness. The patient' apnea, and his having been enduring all the distress of apnea, make noise and sleep-difficulty especially distressing.

And to make matters worse, the pneumatic causation of the noise has made it a matter of particular difficulty to sufficiently minimize, for its effective elimination is not a matter of typical noise-reduction techniques, e.g., oiling, shimming, tightening, baffling, capping, etc.

Moreover, the delivery of ample forced air to the apnea patient must inevitably require an openness of communication all the way from the blower which produces objectionable noise as well as the needed air, to the face of the user, an open tube whose capacity to carry the sound waves is a known fact of physics, as is illustrated by the pipes of organs or the pipe-like bores of many types of musical instruments.

Thus, most of the factors of need, and particularities of the difficulties, etc., have been known for many years; yet, although many of the sound or noise problems of blowers and air ducts have been solved, or acceptably minimized, the irritating and patient-bothering distress of blower-caused whine have remained.

SUMMARY OF THE INVENTION

In accordance with the present invention, the high-pitched whine-like sound of blowers is muffled by providing the delivery ducts to and from each of the blower inlet and outlet with a muffler connected to the opening of the blower, and the muffler having a combination of features:

(a) The length of the muffler is provided to be a length according to the following formula:

$$L_1 = N \times \text{one half wave length, plus one quarter wave length};$$

Where "N" is any whole integer, and

Where $L_1$ is the distance from the location of the edge of the blower casing adjacent the path of the blower's impeller to the surface of the sound-absorbing material at the end of the muffler remote from the blower; and Where the wave length is the wave length of the whine-like noise emanating from the blower; and (b) The length of inset of the muffler outlet remote from the blower is provided to be a length according to the following formula:

$L_2$ = one eighth wave length, or $L_2 = N \times$ wave length, plus or minus one eighth wave length;

Where $L_2$ is the length of inset of the centerline of the muffler outlet remote from the blower, to the surface of the sound absorbing material at the end of the muffler remote from the blower; and Where "N" is any whole integer; and Where the wave length is the wave length of the whine-like noise emanating from the blower; and (c) the muffler is lined with sound absorbing material.

Other uses are within the concepts as specified herein, although the invention is herein shown in a forced breathing system.

BRIEF DESCRIPTION OF THE DRAWINGS

The above description of the novel airduct muffler is of somewhat introductory and generalized form. More particular details, concepts, and features are set forth in the following and more detailed description of an illustrative embodiment, taken in conjunction with the accompanying drawings, which are of somewhat schematic and diagrammatic nature, for showing of the inventive concepts and illustrating the use of the components of the invention in this embodiment, portions shown broken away for illustrating details otherwise hidden.

In the drawings:

FIG. 1 is a pictorial view of a muffler device shown as attached to a typical blower, one to each of the blower's inlet and outlet, and showing in dashed lines a motor for the blower in a typical arrangement commercially obtainable, the mufflers being shown with arrows to indicate the inlet of air to the inlet muffler and the outlet of air from the outlet muffler; and FIG. 2 is a longitudinal cross-sectional view of a muffler of the present invention according to the invention or discovery, and shown connected to one of the inlet or outlet ports of the blower housing, with portions of the blower, and its housing impeller, and motor, indicated merely by chain lines;

FIG. 3 is a dimensional representation to illustrate diagrammatically what seem to be significant dimensional relation details of the muffler which according to the present invention or discovery seem to provide the basis for the operational characteristics of noise-muffling here achieved; and the placement of FIG. 3 on the paper is purposefully adjacent FIG. 2 and longitudinally aligned with the muffler of FIG. 2 as a dimensional representation of those details.

DETAILED DESCRIPTION OF THE EMBODIMENT SHOWN

As shown in the drawings, an inlet muffler 10 and an outlet muffler 12 are shown respectively connected to the inlet 14 and outlet 16 of a blower 18 of a typical blower assembly 19 having a motor 20 which drives an impeller 22.

The blower's impeller 22 is schematically indicated, and is revolvable on bearings (not shown) in a casing 24, the impeller chamber 25 being shown as having a back edge 26 and an edge 28 adjacent the casing's inlet 14 and outlet 16; and it is believed that the source of the blower's objectionable whine-like noise is at the location of the passage of the blades of the impeller 22 rapidly past the inlet 14 and outlet 16.

A support collar 30 is tightly pressed into a recess 32 in the housing casing 24, and is suitably held therein as by tack welds 32a, the recess 32 being concentric with the inlet 14 or outlet 16, both having such a collar 30.

Each collar 30 is lined interiorly with sound-absorbing material 33; and each collar 30 is provided exteriorly with a holder body 34 which provides annular recess 36 into which may be slipped the inner end 38 of the muffler body 10 or 12.

Turning now to the details of the muffler bodies 10 and 12, each has a generally cylindrical shell 40; and the shell 40 is lined interiorly with sound-absorbing material 42 throughout its entire length, desirably of a thickness such that its inner end 44 is substantially flush with the outer end 46 of the lining 33 of the collar 30.

The outer end 48 of the muffler shell 40 is capped by a cap 50, and the cap 50 also is lined interiorly with sound-absorbing material 52.

The muffler's outlet duct 54 which is adjacent the end 48 of the muffler body 40 remote from the blower 18 (and thus the component 54 is called an "outlet" whether on the inlet muffler 10 or the outlet muffler 12) is on an axis 55 perpendicular to the axis of the muffler body 40, and is inset from the cap 50 end of the muffler 10/12, as detailed below.

The overall sound-minimizing effect of the invention is contributed by the features of the sound-absorbing linings 33, 42, and 52, of the collar 30, muffler body 40, and end cap 50, respectively, and by providing that the muffler features are co-ordinated with the wave length of the whine-like blower sound, more particularly as follows, for reasons which are believed to be the relationships illustrated in FIG. 3.

That is, as one factor, the length "$L_1$" of the muffler body 40 is provided to be a length according to the following formula:

$L_1 = N \times$ one half wave length, plus one quarter wave length;

Where "N" is any whole integer, which of course has to be numerically high enough that the outlet duct 54 is remote enough from the blower 18 so as to not be blocked by the motor 20 of the embodiment of the drawings or an other nearby obstacle, and Where $L_1$ is the distance from the location of the edge 28 of the blower casing 24 adjacent the path of the blower's impeller 22 to the surface 56 of the sound-absorbing material 52 at the end of the muffler 40 remote from the blower 18, and Where the wave length is the wave length of the whine-like noise emanating from the blower 18.

Further, as shown by the relationship shown in FIG. 3, the length "$L_2$" of inset of the muffler outlet 54 remote from the blower 18 is provided to be a length according to the following formula:

$L_2$ = one eight wave length, or $L_2 = N \times$ wave length, plus or minus one eighth wave length;

Where $L_2$ is the length of inset of the centerline 55 the muffler outlet 54 remote from the blower 18, to the surface 56 of the sound absorbing material 52 at the end of the muffler 40 remote from the blower 18, and Where "N" is any whole integer, it being small enough numerically that the outlet 54 is not blocked by the blower motor 20, as in the illustrative embodiment shown in the drawings, or any other obstacle nearby to the mufflers 10/12, and Where the wave length is the wave length of the whine-like noise emanating from the blower 18.

The reasons believed to be the cause of the effectiveness of these relationships are that the "$L_1$" distance per the above analysis places the surface 56 at a location of minimal sound-wave amplitude, thus to deflect only a minimal amount of noise into the duct 54. Also, the "$L_2$" distance per the above analysis places the outlet duct 54 at a location to be at least an amplitude "A" less than maximum amplitude, yet not be so close to the end wall 56 to get an undue amount of the transverse components of what are the components of sound which are deflected off the wall 56; or, of "N" is larger, as would be possible if the motor 20 was not an obstacle, a location of the duct 54 would per this analysis provides "$L_2$" to be such that the amplitude of the whine-sound would be minimum or no more than the relatively low amplitude "B".

It is to be noted that the outlet 54 (whether on the inlet muffler 10 or outlet muffler 12, as noted above) and its axis 55 are generally perpendicular to the general axis of the muffler shell or body 40. This is believed to provide that the combination effect of sound waves bouncing off the end wall 56 of body 40, and waves traveling along the body 40, have minimal effect in carrying the objectionable rotor whine noise from the muffler into ductwork (not shown) leading to the associated equipment such as the patient's breathing apparatus (not shown) as leads from the outlet muffler 12, or similarly to the ductwork or inlet openings for the inlet admission of air to the blower 18 through inlet muffler 10.

This minimization of noise waves into the outlets 54 is believed to co-operate with the other relationships herein set forth, particularly that of the distance "$L_2$" to minimize objectional noise emanating from the muffler 10/12.

CONCLUSION

Is thus seen that a muffler means, constructed and used according to the inventive concepts herein set forth, provides novel concepts of a desirable and advantageous device, yielding the advantages of a muffler which quite useful effectively silencing the very bothersome and annoying whine-like sound of the blower of a forced air system for positive air pressure, especially helpful for patients suffering the perils and distress of respiratory disorders such as apnea.

In summary as to the nature of these advantageous concepts, their inventiveness is shown by novel features of concept and construction shown herein, and by the novel concepts hereof not only being different from all the prior art known, but because the achievement is not what is or has been suggested to those of ordinary skill in the art, especially realistically considering this as comprising components surely well known to most muffler manufacturers and pneumatic system manufacturers, for scores of years the entire world over. No prior art has suggested the modification of any prior art to achieve the novel concepts here achieved, even though sound-muffing in a pneumatic system, as a general concept, has been known as to many types of devices or installations using pneumatic pressure lines.

Accordingly, it will thus be seen from the foregoing description of the invention according to this illustrative embodiment, considered with the accompanying drawings, that the present invention provides new and useful concepts of a novel and advantageous muffler means having and yielding desired advantages and characteristics in construction and use, and accomplishing the intended objects, including those hereinbefore pointed out and others which are inherent in the invention.

Modifications and variations may be effected without departing from the scope of the novel concepts of the invention; accordingly, the invention is not limited to the specific embodiment, or form or arrangement of parts herein described or shown.

And although a medical use of forced air breathing is a particularly-envisioned use of the concepts, they provide sound-minimizing operativity for other muffler installations; and thus the concepts are to not be considered to be limited to apnea therapy nor to only medical uses, nor even to uses in which the output of the muffler is used at all.

Nor are the concepts limited even to uses in which the muffler discharges into a duct, especially since it has been mentioned that it is not only an output muffler but also an input muffler which is silenced by these concepts.

I claim:

1. A set of mufflers for operative connection to a blower having a housing which has an inlet and an outlet, each providing an opening into the housing, and the housing having an impeller which has revolvable movement in the housing along a path of rotation, the housing having both outlet and inlet edges which are respectively adjacent the path of the impeller, and the blower emanates a whine-like sound as the impeller is moving in said revolvable movement in the housing;

each of the mufflers having a housing, and having a first end and a second end, a first one of said ends of each muffler being the end for operative connection to the blower housing inlet and outlet, respectively, and the second end of each muffler being remote from the blower housing;

sound-absorbing material being provided as to each muffler, respectively, at the second end of the muffler, and having a surface facing the said first end of the respective muffler;

and each of the muffler housings are provided to have a length according to the follwing formula:

$L_1 = N \times$ one half wave length, plus one quarter wave length;

where "N" is any whole integer;

where $L_1$ is the distance from the outlet and inlet edges of the blower housing adjacent the path of the impeller to the said surface of the sound-absorbing material at the said second end of the respective muffler; and where the wave length is a wave length of the whine-like noise emanating from the blower.

2. A set of mufflers for operative connection to a blower having a housing which has an inlet and an outlet, each providing an opening into the housing, and the housing having an impeller which has revolvable movement in the housing along a path of rotation, the housing having both outlet and inlet edges which are respectively adjacent the path of the impeller, and the blower emanates a whine-like sound as the impeller is moving in said revolvable movement in the housing;

each of the mufflers having a housing, and having a first end and a second end, a first one of said ends of each muffler being the end for operative connection to the blower housing inlet and outlet, respectively, and the second end of each muffler being remote from the blower housing;

sound-absorbing material being provided as to each muffler, respectively, at the second end of the muffler, and having a surface facing the said first end of the respective muffler;

and the muffler connectable to the blower housing inlet, and the muffler connectable to the blower housing outlet, respectively, having an inlet and an outlet, respectively, remote from the blower, the said inlet and outlet of each respective muffler being inset from the said surface of the sound-absorbing material, and having a centerline, and each muffler being provided to have a distance of the inset of the muffler inlet centerline and outlet centerline, respectively, from the said surface of sound-absorbing material, to be provided to be the distance according to the following formula:

$L_2$ = one eighth wave length;

or $L_2$ = N × wave length, plus or minus one eighth wave length;

where $L_2$ is the distance of the inset of the centerline of the muffler inlet and outlet, respectively, remote from the blower, to the said surface of the sound-absorbing material at the said second end of the respective muffler remote from the blower; and where "N" is any whole integer; and where the wave length is a wave length of the whine-like noise emanating from the blower.

3. The invention as set forth in claim 1, wherein the muffler connectable to the blower housing inlet, and the muffler connectable to the blower housing outlet, respectively, having an inlet and an outlet, respectively, remote from the blower, the said inlet and outlet of each respective muffler being inset from the said surface of the sound-absorbing material, and having a centerline, and each muffler being provided to have a distance of the inset of the muffler-inlet centerline and outlet centerline, respectively, from the said surface of sound-absorbing material, to be provided to be the distance according to the following formula:

$L_2$ = one eighth wave length;

or $L_2$ = N × wave length, plus or minus eighth wave length;

where $L_2$ is the distance of the inset of the centerline of the muffler inlet and outlet, respectively, remote from the blower, to the said surface of the sound-absorbing material at the said second end of the respective muffler remote from the blower; and where "N" is any whole integer; and where the wave length is a wave length of the whine-like noise emanating from the blower.

4. The invention as set forth in claim 1, in which the muffler housings each have an interior wall, and the mufflers are each lined with sound-absorbing material along said interior wall.

5. The invention as set forth in claim 2, in which the muffler housings each have an interior wall, and the mufflers are each lined with sound-absorbing material along said interior wall.

6. The invention as set forth in claim 3, in which the muffler housings each have an interior wall, and the mufflers are each lined with sound-absorbing material along said interior wall.

7. The invention as set forth in claim 1, in which, as to each of the housing inlet and outlet openings to be provided with a muffler, there is provided a collar to which the respective muffler may be fastened, and the blower housing is provided with a recess into which the respective collar fits.

8. The invention as set forth in claim 1, in which the inlet of the muffler connectable to the blower housing inlet, and the outlet of the muffler connectable to the blower housing outlet, respectively, are on an axis generally perpendicular to that of the respective muffler.

9. The invention as set forth in claim 2, in which the inlet of the muffler connectable to the blower housing inlet, and the outlet of the muffler connectable to the blower housing outlet, respectively, are on an axis generally perpendicular to that of the respective muffler.

10. The invention as set forth in claim 3, in which the inlet of the muffler connectable to the blower housing inlet, and the outlet of the muffler connectable to the blower housing outlet, respectively, are on an axis generally perpendicular to that of the respective muffler.

11. The invention as set forth in claim 4, in which the inlet of the muffler connectable to the inlet of the blower housing, and the outlet of the muffler connectable to the outlet of the blower housing, respectively, is on an axis generally perpendicular to that of the muffler.

12. The invention as set forth in claim 5, in which the inlet of the muffler connectable to the inlet of the blower housing, and the outlet of the muffler connectable to the outlet of the blower housing, respectively, is on an axis generally perpendicular to that of the muffler.

13. The invention as set forth in claim 6, in which the inlet of the muffler connectable to the inlet of the blower housing, and the outlet of the muffler connectable to the outlet of the blower housing, respectively, in on an axis generally perpendicular to that of the muffler.

14. The invention as set forth in claim 7, in which the inlet of the muffler connectable to the inlet of the blower housing, and the outlet of the muffler connectable to the outlet of the blower housing, respectively, is on an axis generally perpendicular to that of the muffler.

* * * * *